United States Patent [19]

France et al.

[11] Patent Number: 5,468,777

[45] Date of Patent: Nov. 21, 1995

[54] METHOD AND AGENTS FOR PREVENTING AND REVERSING THE STAINING OF TEETH

[75] Inventors: Dennis S. France, Morris Plains, N.J.; Anthony Cerami, Shelter Island, N.Y.; Peter C. Ulrich, Old Tappan, N.J.; Laura A. Norton, Ridgewood, N.J.; David L. Neer, Allendale, N.J.

[73] Assignees: The Rockefeller University, New York, N.Y.; Alteon Inc., Ramsey, N.J.

[21] Appl. No.: 236,228

[22] Filed: Apr. 29, 1994

Related U.S. Application Data

[63] Continuation-in-part of Ser. No. 825,598, Jan. 27, 1992, Pat. No. 5,334,617, which is a continuation-in-part of Ser. No. 805,200, Dec. 10, 1991, Pat. No. 5,238,968, which is a division of Ser. No. 481,869, Feb. 20, 1990, Pat. No. 5,128,360, which is a continuation-in-part of Ser. No. 220,504, Jul. 18, 1988, abandoned, which is a division of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.[6] ............... A61K 31/195; A61K 31/155; A61K 7/16
[52] U.S. Cl. ............... 514/562; 424/49; 514/635
[58] Field of Search ............... 424/79; 514/562, 514/635

[56] References Cited

U.S. PATENT DOCUMENTS

| | | | |
|---|---|---|---|
| 3,055,882 | 9/1962 | Mull et al. | 260/239 |
| 3,055,883 | 9/1962 | Mull et al. | 260/239 |
| 3,098,066 | 7/1963 | Mull et al. | 260/239 |
| 3,101,336 | 8/1963 | James et al. | 260/268 |
| 3,178,433 | 4/1965 | Mull et al. | 260/268 |
| 3,506,680 | 4/1970 | Berger et al. | 424/326 |
| 3,637,850 | 1/1972 | Houlihan et al. | 260/564 F |
| 3,681,504 | 8/1972 | Johnston et al. | 424/326 |
| 3,746,764 | 7/1973 | Nordmann et al. | 260/564 F |
| 4,665,192 | 5/1987 | Cerami | 548/336 |
| 4,758,583 | 7/1988 | Cerami et al. | 514/399 |
| 4,908,446 | 3/1990 | Ulrich et al. | 540/553 |
| 4,978,684 | 12/1990 | Cerami et al. | 514/632 |
| 4,983,604 | 1/1991 | Ulrich et al. | 514/238.5 |
| 5,096,703 | 3/1992 | Cerami et al. | 424/54 |
| 5,128,122 | 7/1992 | Cerami et al. | 424/49 |
| 5,286,480 | 2/1994 | Boggs et al. | 424/54 |
| 5,334,617 | 8/1994 | Ulrich et al. | 514/562 |

FOREIGN PATENT DOCUMENTS

| | | |
|---|---|---|
| 61037/80 | 8/1981 | Australia . |
| 64958/86 | 8/1987 | Australia . |
| 0111211 | 6/1984 | European Pat. Off. . |
| 0222313 | 5/1987 | European Pat. Off. . |
| 0316852 | 5/1989 | European Pat. Off. . |
| 0370994 | 5/1990 | European Pat. Off. . |
| 0372603 | 6/1990 | European Pat. Off. . |
| 45-27114 | 9/1970 | Japan . |
| 54-138136 | 10/1979 | Japan . |
| 60-118174 | 6/1985 | Japan . |
| 60-27371 | 21/1985 | Japan . |
| 62-142114 | 11/1987 | Japan . |
| 64-56614 | 3/1989 | Japan . |
| 134099 | 11/1969 | Switzerland . |
| 809165 | 2/1959 | United Kingdom . |

OTHER PUBLICATIONS

Martindale, The Extra Pharmacopoeia, 28th Ed., The Pharmaceutical Press, 1982, pp. 50 and 554–556.
Bain. 1980. "Chlorhexidine in dentistry—a review," *New Zealand Dental Journal.* 76: 49–54.
Baylin et al. 1975. "Increase in food consumption and growth after treatment with aminoguanidine." *Experientia* 31: 562–4.
Beavin et al. 1969. "A specific and sensitive assay for aminoguanidine: its application to a study of the disposition of aminoguanidine in animal tissues." *J. Pharm Exp. Ther.* 165: 14–22.
Brown et al. 1990. "Aminoguanidine prevents cataracts in the nephrectomized alloxan—induced diabetic rabbit," *J. Am. Soc. Nephrol.* 1(4): 329, 8P.
Brownlee. 1989. "Pharmacological modulation of the advanced glycosylation reaction." *Chem. Abstracts* 111: 70141f.
Brownlee et al. 1988 "Advanced glycosylation end products in tissue and the biochemical basis of diabetic complications," *No. Eng. J. Med.* 318: 1315–21.
Brownlee et al. 1986. "Inhibition of glucose—derived protein crosslinking and prevention of early diabetic changes in glomerular basement membrane by aminoguanidine." *Diabetes* 35, supp. 1: 42A, 166.
Brownlee et al. 1986. "Aminoguanidine prevents diabetes—induced arterial wall protein cross–linking," *Science* 232: 1629–32.
Brownlee et al. 1985. "Nonenzymatic glycosylation products on collagen covalently trap low–density lipoprotein," *Diabetes* 34: 938–41.
Brownlee et al. 1984. "Nonenzymatic glycosylation and the pathogenesis of diabetic complications", *Ann. Int. Med.* 101: 527–37.
Brownlee et al. 1983. "Covalent attachment of soluble proteins by nonenzymatically glycosylated collagen," *J. Exp. Med.* 158: 1730–1744.
Bunn et al. 1975. "Further identification of the nature and linkage of the carbohydrate in hemoglobin $A_{1c}$." *Biochem. Biophys. Res. Comm.* 67: 103–9.
Cameron et al. 1992. "Effects of aminoguanidine on peripheral nerve function and polyol pathway metabolites in streptozotocin—diabetic rats." *Diabetologia* 35: 946–50.
Carroll et al. 1984. "Dose—dependent inhibition of aortic (List continued on next page.)

Primary Examiner—Kimberly R. Jordan
Attorney, Agent, or Firm—Klauber & Jackson

[57] ABSTRACT

The present invention relates to methods and agents for preventing and reversing the staining of teeth caused by the nonenzymatic browning of proteins in the oral cavity. Suitable agents for the inhibition of nonenzymatic browning may be formulated as rinses and toothpastes, and include cysteine and cysteine derivatives. These preparations may further include known anti-plaque agents, such as chlorhexidine.

11 Claims, 6 Drawing Sheets

OTHER PUBLICATIONS albumin in diabetes by alpha—hydrazinohistidine." *Fed. Proc.* 43: 2514.

Ceriello et al. 1985. "Acetylsalicylic acid amd lysine inhibit protein glycosylation in vitro." *Chem. Abstracts* 103: 115893f.

Dabrowski et al. 1984. "Alterations in histamine and collagen induced in chick embryos by aminoguanidine and 48/80." *Agents and Actions* 14: 458–60.

Dabrowski et al. 1983. "The effects of the stimulation of histamine–forming capacity (HFC) and the inhibition of histamine catabolism on tensile and collagen content of skin wounds in the rats." *Acta. Physiol. Pol.* 34: 91–7.

Eble et al. 1983. "Nonenzymatic glucosylation and glucose–dependent cross–linking of protein." *J. Biol. Chem.* 258: 9406–12.

Geisen, 1987. "Influence of aminoguanidine on cataract development in streptozotocin–diabetic rats." *Akt. Endocrin. Stoffw.* 8: 78.

Giambrone and Brownlee. 1989. "Aminoguanidine treatment normalizes increased steady–state levels of laminin B1 mRNA in kidneys of long–term streptozocin–diabetic rats." *Diabetes* 38, Supp. 2: 83 A.

Godfrey. 1962. "The synthesis of heterocyclic compounds from urea derivitives." Doctoral Dissertation. University of London.

Harding. 1985. "Nonenzymatic covalent posttranslational modification of proteins in vivo." *Advances in Protein Biochemistry* 37: 247–334.

Hauase et al. 1989. "Aging of proteins: immunological detection of a glucose–derived pyrrole formed during Maillard reaction in vivo." *J. Biol. Chem.* 263: 3758–64.

Hollis and Strickberger. 1985. "Inhibition of aortic histamine synthesis by alpha–hydrazinohistadine inhibits increased aortic albumin accumulation in experimental diabetes in the rat." *Diabetologia* 28: 282–5.

Hollis et al. 1095. "Changes in plasma histamine concentration in the streptozotocin–diabetic rat." *Exp. Molec. Path.* 43: 90–6.

Hollis et al. 1984. "Time–dependent changes in aortic albumin permeability characteristics in experimental diabetes." *Exp. Molec. Path.* 41: 207–17.

Hollis et al. 1984. "Aortic albumin accumulation in diabetes and hypertension and its alteration by alpha–hydrozinahistidine, insulin and hypertension reversal." *Fed. Proc.*43: 714, 2513.

Hull. 1980. "Chemical inhibition of plaque." *J. Clin. Periodont.* 7: 431–42.

Khatami et al. 1988. "Inhibitory effects of pyridoxal phosphate, ascorbate and aminoguanidine on nonenzymatic glycosylation." *Chem. Abstracts* 110: 643b.

Kihara et al. 1991. "Aminoguanidine effects on nerve blood flow, vascular permeability, electrophysiology, and oxygen free radicals." *Proc. Natl. Acad. Sic.* USA 88: 6107–6111.

Kohn et al. 1984. "Collagen aging in vitro by nonenzymatic glycosylation and browning." *Diabetes* 33: 57–9.

Kumari et al. 1991. "Inhibition of diabetes–associated complications by nucleophilic compounds," *Diabetes* 40: 1079–84.

Lehninger. 1981. "Proteins: three–dimentional conformation," *Biochemistry: The Molecular Basis of Cell Structure and Function.* 2nd ed pp. 135–6.

Levine and Watts. 1966. "A sensitive and specific assay for histidine decarboxylase activity." *Biochem. Pharmac.* 15: 841–9.

Levine and Noll. "Histidine decarboxylase and its inhibition." *Ann. N.Y. Acad. Sci.* : 246–56 (1969).

Lewis and Harding. 1990. "The effects of aminoguanidine on the glycation (non–dnzymic glycosylation) of lens proteins." *Exp. Eye Res.* 50: 463–67.

Lindberg and Tornqvist. 1966. "The inhibitory effect of aminoguanidine on histamine catabolism in human pregnancy." *Acta. Obst. Gyn Scand.* 45: 131–9.

Lubec et al. 1990. "The effect of substance L on glucose–mediated cross–links of collagen in the diabetic db/db mouse." *Nephron* 56: 281–4.

*Merck Index.* 1989. 11th ed. entry #'s 441, 453, 2787, 5509, 6826, 7029.

*Merck Index.* 1983. 10th ed. entry #444.

*Merck Index.* 1976. 9th ed. entry #'s 447, 4676.

Monnier et al. 1984. "Accelerated age–related browning of human collagen in diabetes mellitus." *Proc. Natl. Acad. Sci.* USA 81: 583–7.

Monnier and Cerami. 1981. "Nonenzymatic browning in vivo: possible process for aging of long–lived proteins." *Science* 211: 491–3.

Nakamura et al. 1991. "Prevention and reversible solubilization of advanced glycation and products (AGE) by organic germanium compounds as derivitives of amino acids." *Amino Acids* 1: 263–78.

Nicholls and Mandel. 1989. "Advanced glycosylation end–products in experimental murine diabetic nephropathy." *Lab. Invest.* 60: 486–91.

Nordbo. 1978. "Ability of chlorhexidine and benzalkonium chloride to catalyze browning reactions in vivo." *J. Dent. Res.* 58: 1429.

Odetti et al. 1990. "Prevention of diabetes–increased aging effect on rat collagen–linked fluorescence by aminoguanidine and rutin." *Diabetes* 39: 796–801.

Oimomi et al. 1989 Letter to the editor re: Aminoguanidine inhibits 3–deoxyglucosone during the advnced Maillard reaction. *Diabetes Res. Clin. Prac.* '6: 311–3.

Oimomi et al. 1989 "The effects of aminoguanidine on 3–deoxyblocosone in the Maillard reaction." *Agric. Biol. Chem.* 53: 1727–8.

Onada et al. "Inhibitors (e.g. aminoguanidines, etc.) of the Maillard reaction and formulations containing them." *Chem. Abstracts* 112: 42594h. (1990).

Orlidge et al. 1992. "Aortic endothelial and smooth muscle histamine metabolism in experimental diabetes." *Arteriosclerosis* 2: 142–50.

Owens et al. 1981. "Local aortic histamine metabolism and albumin accumulation." *Arteriosclerosis* 1: 265–72.

Oxlund et al. 1992. "Aminoguanidine treatment redices the increase in collagen stability of rats with experimental diabetes mellitus." *Diabetologia* 35: 19–25.

Oxlund et al. 1989. "The increase in biochemical and biomechanical stability of collagen in diabetic rats is prevented by aminoguanidine treatment." European Assn. for the Study of Diabetes, 25th Annual Meeting, p. 525A, abstract #371.

Pongor et al. 1984. "Aging of proteins: isolation and identification of a fluorescent chromophore from the reaction of polypeptides with glucose." *Proc. Natl. Acad. Sci.* USA 81: 2684–8.

Soulis–Liprota et al. 1991. "Retardation by aminoguanidine of development of albuminuria, mesangial expansion, and tissue fluorescence in strepotozocin–induced diabetic rat." *Diabetes* 40: 1328–34.

Sell and Monnier. 1989. "Structure elucidation of a senescence cross-link from a human extracellular matrix." *J. Biol. Chem.* 264: 21597–602.

Suarez et al. 1988. "Administration of an aldose reductase inhibitor induces a decrease of collagen fluorescence in diabetic rats." *J. Clin Invest.* 82: 624–27.

Tonelli et al. 1983. "Chlorhexidine: a review of the literature." *J. Western Soc. Periodont./Periodont. Abs.* 31: 5–10.

METHOD AND AGENTS FOR PREVENTING AND REVERSING THE STAINING OF TEETH

This Application is a continuation-in-part of U.S. application Ser. No. 07/825,598, filed Jan. 27, 1992, now U.S. Pat. No. 5,334,617; which is a continuation-in-part of U.S. Ser. No. 07/805,200, filed Dec. 10, 1991 and now U.S. Pat. No. 5,238,968; which is a Division of U.S. Ser. No. 07/481,869, filed Feb. 20, 1990, and now U.S. Pat. No. 5,128,360; which is a continuation-in-part of U.S. Ser. No. 07/220,504, filed Jul. 18, 1988 and now abandoned; which is a Division of U.S. Ser. No. 06/798,032 filed Nov. 14, 1985 and now U.S. Pat. No. 4,758,583, which is a continuation-in-part of U.S. Ser. No. 06/590,820, filed Mar. 19, 1984 and now U.S. Pat. No. 4,665,192. Applicants claim the benefits of these Applications under 35 U.S.C. §120.

BACKGROUND OF THE INVENTION

The present invention relates generally to the reaction that occurs between glucose and proteins, and more particularly to the inhibition by cysteine and cysteine derivatives of the reaction of nonenzymatically glycosylated proteins leading to advanced glycosylation end products.

The nonenzymatic browning reaction which occurs in the oral cavity results in the discoloration of teeth and tongue. Presently used anti-plaque agents accelerate this nonenzymatic browning reaction and further the staining of the teeth and tongue.

The appeal of a perfect smile composed of pearly-white teeth is undeniable. Many dollars are spent to achieve this appearance, and the natural discoloration which occurs on the tooth surfaces often becomes quite noticeable in many individuals. Tooth discoloration is also greatly accelerated in most individuals who use certain anti-plaque agents to prevent oral disease. The purpose of the present invention is to provide a method and agents for preventing the discoloration which occurs on the tooth surface as a result of nonenzymatic browning, both naturally and as a result of the use of anti-plaque agents. As used herein, "tooth" and "teeth" refer to both naturally occurring and artificial teeth, artificial tooth surfaces and restorations.

Dental caries, gingivitis and periodontal disease are widespread and affect nearly all individuals to some extent cosmetically, medically, and financially. These conditions arise from the action of certain microorganisms, principally bacteria, which colonize surfaces in the mouth and whose action lead to demineralization of bone, resulting in caries, and chronic irritation and infection of gum tissue (gingivitis) especially in pockets surrounding the teeth, leading to periodontal disease. The results of both processes can be painful, disfiguring and psychologically debilitating.

The development of tooth and gum disease is a complex process involving contributions from the tooth and gum surface, components and properties of saliva, diet, and the numerous species of bacteria present in the mouth, as well as many other factors. Generally, incubation of a newly cleaned tooth surface in the mouth initially results in the deposition on the surface of a material called pellicle, which is composed of protein and polysaccharide derived from saliva and bacterial cells. As colonizing bacteria grow, they produce a polysaccharide from the decomposition of food sugars. This polysaccharide favors the attachment of the bacteria to the tooth surface and also favors mineralization of calcium salts from saliva in the pellicle. As the process continues, the bacterial mass known as plaque becomes a focus for demineralization of bone and irritation of tissues. Acids produced by bacteria during food sugar fermentation dissolve bone, and the plaque mass prevents buffers in saliva from neutralizing these acids. The result is dental caries. The bacteria in plaque and those residing in pockets surrounding teeth produce endotoxin and other well-known bacterial products which are intensely irritating to tissues and cause the tissues to react, resulting in recession of gum tissue, demineralization of bone, and localized irritation.

One of the consequences of long-term exposure of proteins in the pellicle and plaque to sugars in the mouth is the process of nonenzymatic browning, which results in discoloration of the tooth surface. Nonenzymatic browning, also known as the Maillard reaction, has been well studied by food chemists since it is responsible for the brown color which forms during the cooking and long-term storage of foods. In this reaction, amino groups in food proteins and other molecules react with sugars in food proteins and other molecules react with sugars to form covalent adducts which undergo rearrangements and result in highly polymerized, colored products. While this process is well-known in food, only recently was its significance realized as concerns the human body and consequences of the long-term exposure of glucose to amino groups on proteins and other macromolecules in the body. The Maillard reaction in vivo has been studied extensively in the last few years and nonenzymatic browning and cross-linking of proteins in vivo has been shown to be an important mechanism by which the sequelae of diabetes and aging arise (see M. Brownlee et al., "Nonenzymatic glycosylation and the pathogenesis of diabetic complications," *Annals of Internal Medicine*, 101, pp. 527–537 (1986)). Elevated glucose levels in diabetes leads more rapidly to consequences involving permanent cross-linking of proteins, yet the normal glucose levels in non-diabetics eventually leads to the same complications.

Methods to prevent nonenzymatic browning in vivo with agents such as aminoguanidine and other inhibitors have been studied (Brownlee et al., "Aminoguanidine prevents diabetes-induced arterial wall protein cross-linking," *Science*, 232, pp. 1629–1632 (1986)), Cerami et al., U.S. Pat. No. 4,798,583; and U.S. Pat. No. 5,128,360.

For many years certain agents have been tested and used to reduce the extent of oral diseases including dental caries, gingivitis and periodontal disease. Regular brushing and flossing apparently are inadequate, at least to the extent practiced by the average individual. Abrasive agents such as silica have been incorporated into toothpastes to attempt to physically remove plaque by enhancing the effectiveness of brushing. Anti-microbial agents have been formulated in oral rinses for regular use to kill bacteria in the mouth. Such agents include sanguinarine, an extract from the bloodroot, which kills certain oral bacteria; certain forms of active peroxide for killing microorganisms; rinses containing alcohol and other ingredients and, more recently, a class of cationic anti-microbial agents with remarkable anti-plaque properties.

These latter agents, the cationic antiseptics, include such agents as alexidine, cetyl pyridinium chloride, chlorhexidine [N,N"-bis(4-chlorophenyl)-3,12-diimino- 2,4,11,13-tetraazatetradecane diimidamide] gluconate, hexetidine, and benzalkonium chloride. Many have been tested for efficacy but one, chlorhexidine, has shown the greatest promise as an anti-plaque agent of low toxicity (see Hull, "Chemical Inhibition of Plaque," *J clin Periodontol.*, 7, pp. 431–432 (1980); Bain, "Chlorhexidine in Dentistry: A Review," *New England and Dent. J.*, 76, pp. 49–54 (1980); Tonelli et al., "Chlorhexidine: A Review of the Literature," *J. West. Soc Periodent.*, 31, pp. 5–10 (1983), and has recently become available in the United States in a prescription formulation known as Periodex ® which contains a 0.12% chlorhexidine gluconate in a solution of water, alcohol, glycerine, flavoring, sweetening and coloring agents.

Chlorhexidine gluconate (CHX), formulated in such a rinse, has been used as a safe and effective therapeutic agent against the bacteria responsible for gingivitis. Use of mouthwashes containing CHX can retard the progression of gum disease, a major cause of gum disease. Unfortunately, the use of CHX-containing mouthwashes often leads to the unsightly discoloration of both the teeth and the tongue. While this side effect is of no medical concern, it is of extreme psychologic concern because stained teeth look ugly and project an undesirable image to others. Likewise, patient compliance is often markedly reduced when such staining becomes evident.

Tooth staining by chlorhexidine and other anti-plaque agents apparently results from the enhancement of the Maillard reaction. Nordbo, *J. Dent. Res*, 58, p. 1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products. Thus, there exists a need for preventing the staining caused by chlorhexidine gluconate and other cationic mouth rinses which will not interfere with their potent anti-microbial and resulting anti-plaque activity.

Ulrich, Cerami and Yamin, in U.S. Pat. Nos. 4,978,684, 5,096,703 and 5,128,122 have described various agents which, by virtue of their ability to inhibit the formation of advanced glycosylation endproducts, also prevent the undesirable tooth-staining by chlorhexidine and similar anti-plaque agents. However, these agents suffer from the drawback that while they prevent tooth-staining, they are ineffective in reversing existing chlorhexidine-accelerated staining.

SUMMARY OF THE INVENTION

In accordance with the present invention, a method of inhibiting and reversing the staining of teeth caused by the nonenzymatic browning of proteins in the oral cavity is disclosed. In particular, the cysteine and cysteine derivatives of formula I can be used for the inhibition and reversal of nonenzymatic browning when formulated as rinses and toothpaste, or in combination with known anti-plaque agents, such as chlorhexidine.

The agents which can be utilized in the methods and formulations of this invention are cysteine and cysteine derivatives. These agents are capable of reacting with a carbonyl moiety of an early glycosylation product formed by the initial glycosylation of the target protein in the nonenzymatic browning reaction. Additionally, these agents are believed to exert their unique and enhanced anti-staining activity by virtue of their activity as reducing agents since their activity as inhibitors of advanced glycosylation does not explain their potency in this regard.

Specific agents utilizable in the present invention are cysteine and cysteine derivatives having the structural formula I $$HS-CH_2-\underset{\underset{NHR}{|}}{CH}-COOH \qquad (I)$$

wherein R is hydrogen or an acyl group; and their pharmaceutically acceptable salts.

The compounds of this invention appear to react with the glycosylation product thereby preventing the same from later forming the advanced glycosylation end products of nonenzymatic browning which result in the discoloration of the teeth in the oral cavity. Additionally, they have been found to reverse existing discoloration resulting from the use of anti-plaque agents such as chlorhexidine.

Accordingly, it is a principal object of the present invention to provide a method of inhibiting and reversing the discoloration of teeth resulting from nonenzymatic browning in the oral cavity which comprises administration to a subject in need of such therapy an amount effective to inhibit said discoloration of a composition comprising cysteine or a cysteine derivative of the formula I.

It is also a principal object of the present invention to inhibit and reverse such discoloration induced by, or resulting from, the use of anti-plaque agents such as chlorhexidine.

It is a still further object of the present invention to provide compositions incorporating cysteine and cysteine derivatives adapted for use in the oral cavity according to the aforesaid methods.

It is a still further object of the present invention to provide compositions which include the cysteine or cysteine derivatives of formula I in compositions containing an anti-plaque agent such as chlorhexidine.

Other objects and advantages will become apparent to those skilled in the art from a consideration of the ensuing description which proceeds with reference to the following illustrative drawings.

DETAILED DESCRIPTION OF THE PREFERRED EMBODIMENTS

In accordance with the present invention, methods and associated compositions have been developed which are believed to inhibit and reverse the discoloration of teeth resulting from nonenzymatic browning in the oral cavity and especially browning resulting from the use of anti-plaque agents. In particular, the invention relates to a method of inhibiting and reversing the discoloration of teeth and tongue resulting from anti-plaque agent-accelerated nonenzymatic browning in the oral cavity which comprises administration to a subject in need of such therapy an amount effective to inhibit said discoloration comprising cysteine or a cysteine derivative of the formula I.

In accordance with this method, the cysteine or the cysteine derivative of the formula I are formulated into compositions adapted for use in the oral cavity. Particularly suitable formulations are oral rinses and toothpastes incorporating cysteine and cysteine derivatives of the formula I as the active agent.

In the practice of this invention, conventional formulating techniques are utilized with nontoxic, pharmaceutically acceptable carriers typically utilized in the amounts and combinations that are well-known for the formulation of such oral rinses and toothpastes.

The cysteine or the cysteine derivative of formula I is formulated in compositions in an amount effective to inhibit the formation of advanced glycosylation end products as well as to reverse existing staining. This amount will, of course, vary with the particular agent being utilized, but typically is in the range of 0.01% to 1.0%, by weight, of the particular formulation.

Preferred compounds of formula I for use in the present invention are L-cysteine and N-acetyl-L-cysteine.

In the definition of R in formula I the acyl radicals referred to herein are residues of lower alkyl, aryl and heteroaryl carboxylic acids containing 2–10 carbon atoms. They are typified by acetyl, propionyl, butanoyl, valeryl, hexanoyl and the corresponding higher chain and branched chain analogs thereof. The acyl radicals may also contain one or more double bonds and/or an additional acid functional group, e.g., glutaryl or succinyl. The lower alkyl groups referred to herein contain 1–6 carbon atoms and include methyl, ethyl, propyl, butyl, pentyl, hexyl, and the corresponding branched chain isomers thereof. The heteroaryl groups referred to above encompass aromatic heterocyclic groups containing 3–6 carbon atoms and one or more heteroatoms such as oxygen, nitrogen or sulfur. Particularly preferred is the acyl cysteine derivative wherein R is an acetyl group, i.e., N-acetylcysteine.

The term "aryl" as used herein refers to phenyl and lower alkyl substituted phenyl groups containing 6–10 carbon atoms and substituted by one or more substituent groups selected from among chloro, bromo, fluoro, carboxy, lower alkyl, hydroxy, or lower monoalkylamino, lower dialkylamino, lower alkoxy. The lower alkoxy groups referred to herein contain 1–6 carbon atoms and include methoxy, ethoxy, propoxy, butoxy, pentyloxy, hexyloxy and the correspondiing branched chain isomers thereof.

Cysteine and the cysteine derivatives of formula I useful in the method of the present invention possess an asymmetric carbon atom. Correspondingly, the present invention relates to both the pure L and D chiral forms, as well as to the racemic mixtures thereof.

The cysteine and cysteine derivatives of formula I are capable of inhibiting the formation of advanced glycosylation end products on such target proteins, by reacting with the carbonyl moiety of the early glycosylation product that is formed by the initial glycosylation of the protein.

It is a carbonyl group located near the junction between sugar and protein segments of the early glycosylation product that is theorized to comprise an active site that causes the further cross-linking of the protein to form an advanced glycosylation end product. Thus, the reaction of the compounds of this invention with this carbonyl moiety is believed to inhibit the late stage Maillard effect and at least partially contribute to the anti-staining effects of cysteine and the cysteine derivatives of formula.

Figure 3:
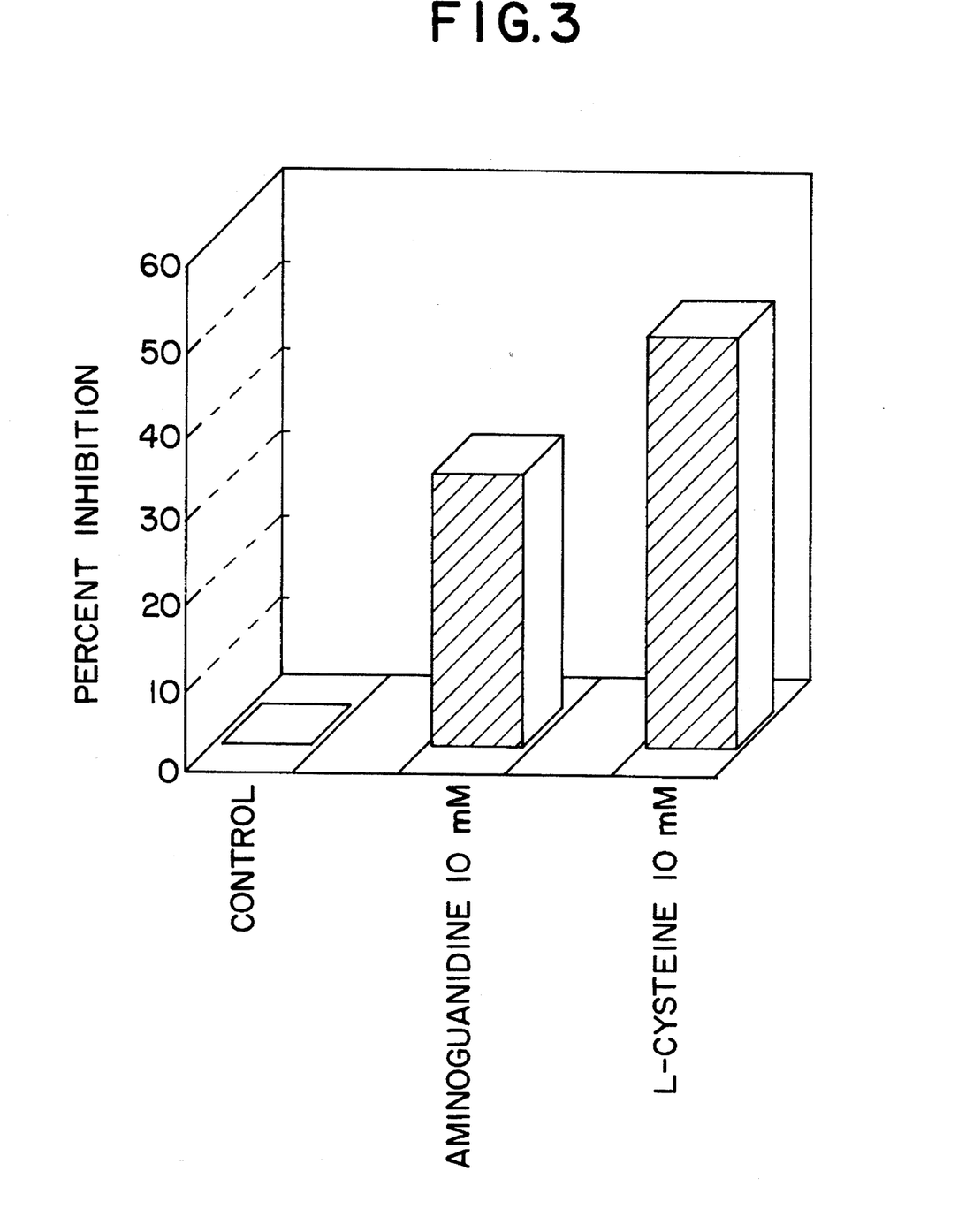
FIG. 3 is a bar graph comparison of the relative activity of aminoguanidine and L-cysteine in an AGE-crosslinking assay.
Figure 4:
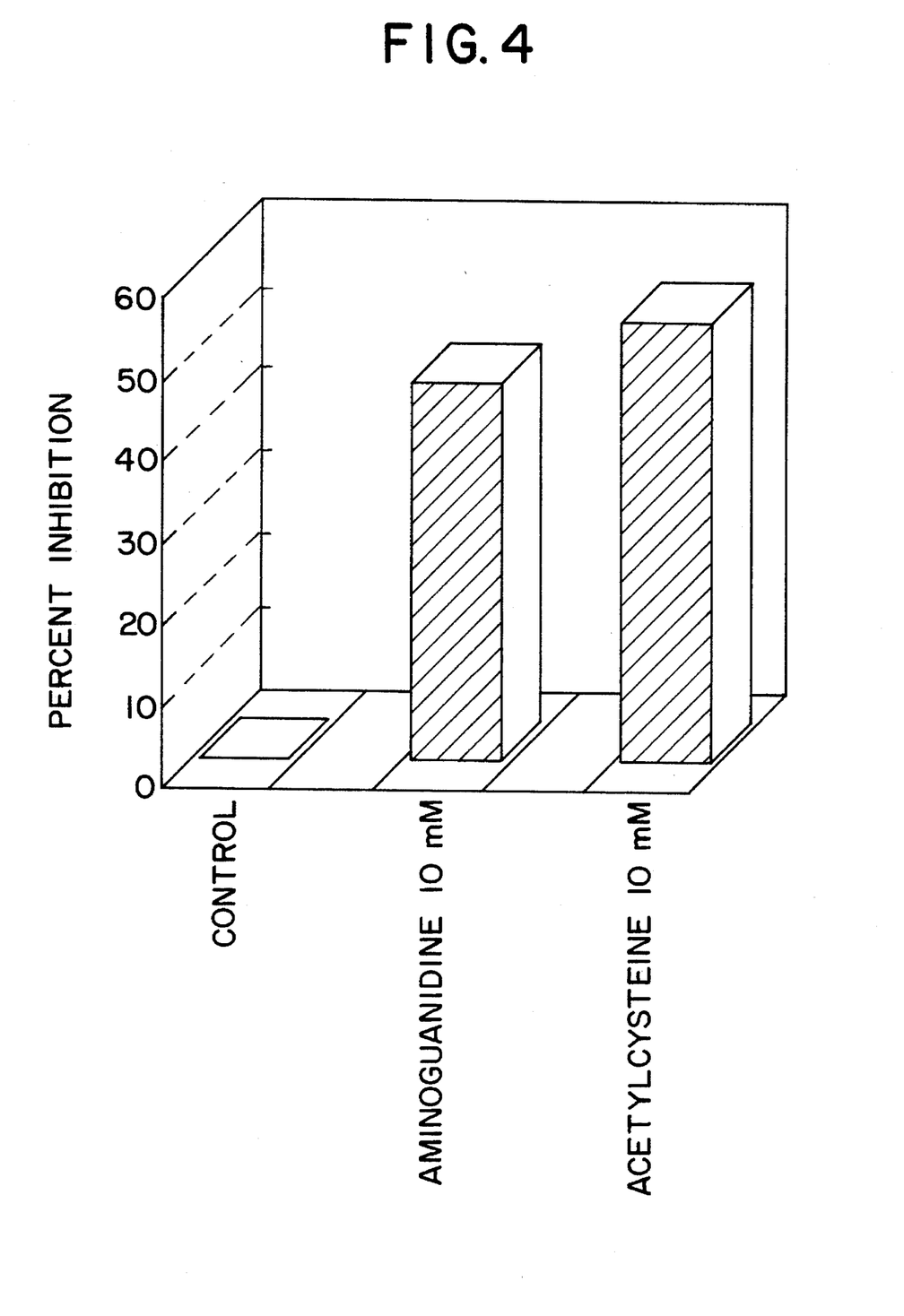
FIG. 4 is a bar graph comparison of the relative activity of aminoguanidine and N-acetyl-L-cysteine in an AGE-crosslinking assay.

It is, however, surprising that cysteine and the cysteine derivatives of formula I possess such enhanced activity vis a vis tooth staining since they are only approximately equal to other known AGE-inhibitions such as aminoguanidine in standardized cross-linking activity. When tested in an immunochemical AGE-crosslinking assay, as illustrated in FIGS. 3 and 4, L-cysteine, N-acetyl-L-cysteine and aminoguanidine are approximately equipotent.

Additionally, aminoguanidine, at concentrations up to 1.0 molar lacks the ability to reverse chlorhexidine-induced tooth staining while both L-cysteine and N-acetyl-L-cysteine exhibit substantially total reversal at this concentration.

Since the composition of the present invention is utilized for in vivo or therapeutic purposes, it is to be noted that the compounds or agents used therein are biocompatible. Pharmaceutical compositions may be prepared with a pharmaceutically effective quantity of the agents or compounds of the present invention and may include a pharmaceutically acceptable carrier, selected from known materials utilized for this purpose. Such compositions may be prepared in a variety of forms, depending on the method of administration. For example, a compound may be converted to the hydrochloride salt from the commercially available bicarbonate salt to improve its solubility and to make it less irritating. Various other pharmaceutically acceptable acid addition salts of the compounds of formulae I, II and III may likewise be utilized. Such acid addition salts may be derived from a variety of organic and inorganic acids such as sulfuric, phosphoric, p-toluenesulfonic, hydrochloric, hydrobromic, hydroiodic, sulfamic, citric, lactic, maleic, succinic, tartaric, cinnamic, acetic, benzoic, gluconic, ascorbic and related acids. Also, a liquid form could be utilized or, if appropriate, tablets, capsules, etc., may be prepared for oral administration.

The cysteine derivatives encompassed by formula I are conveniently prepared by chemical syntheses well known in the art. Certain of the compounds encompassed by formula I are known compounds readily available from chemical supply houses and/or preparable by synthetic methods specifically published therefor.

The following examples detail the methods and compositions utilizable in the present invention.

EXAMPLE 1

The in vitro model of CHX-accelerated tooth staining consists of adsorbing protein for saliva and tongue scrapings to a solid phase support of polyvinylidene difluoride (PVDF, BioRad Labs) membrane. Protein from the tongue and saliva were collected into sterile 50 ml conical test tubes and frozen at −20° C. until used. This preparation was centrifuged at 10,000 g for 10 minutes and the soluble protein supernatant collected, aliquoted and frozen in 1.0 ml aliquots. Such preparations typically contain 5.0 mg/ml total protein. Thawed immediately before use, 10 microliters samples of oral protein were pipetted onto PVDF membrane pre-equilibrated in methanol. The proteins and membranes are allowed to dry under a heat lamp. This application results in uniform circles of 6 mm in diameter. Prior to the assay the membranes are cut into 12 mm squares, each square containing one dot of oral protein. These squares are placed in the wells of 24-well tissue culture plates (Costar). Such plates can be covered with parafilm and incubated for several days without evaporation of liquids in the wells.

CHX-accelerated staining was modelled and optimized under the following conditions:

333 millimolar sodium phosphate buffer, pH 7.4 (Sigma Chem. Co.)

333 millimolar ribose (Sigma Chem. Co.)

0.04% chlorhexidine gluconate (Spectrum Chemical Mfg. Corp.)

96 hours at 37° Celsius in a humidified incubator.

10 ug/ml gentamycin (Schering) to inhibit bacterial growth

Figure 1:
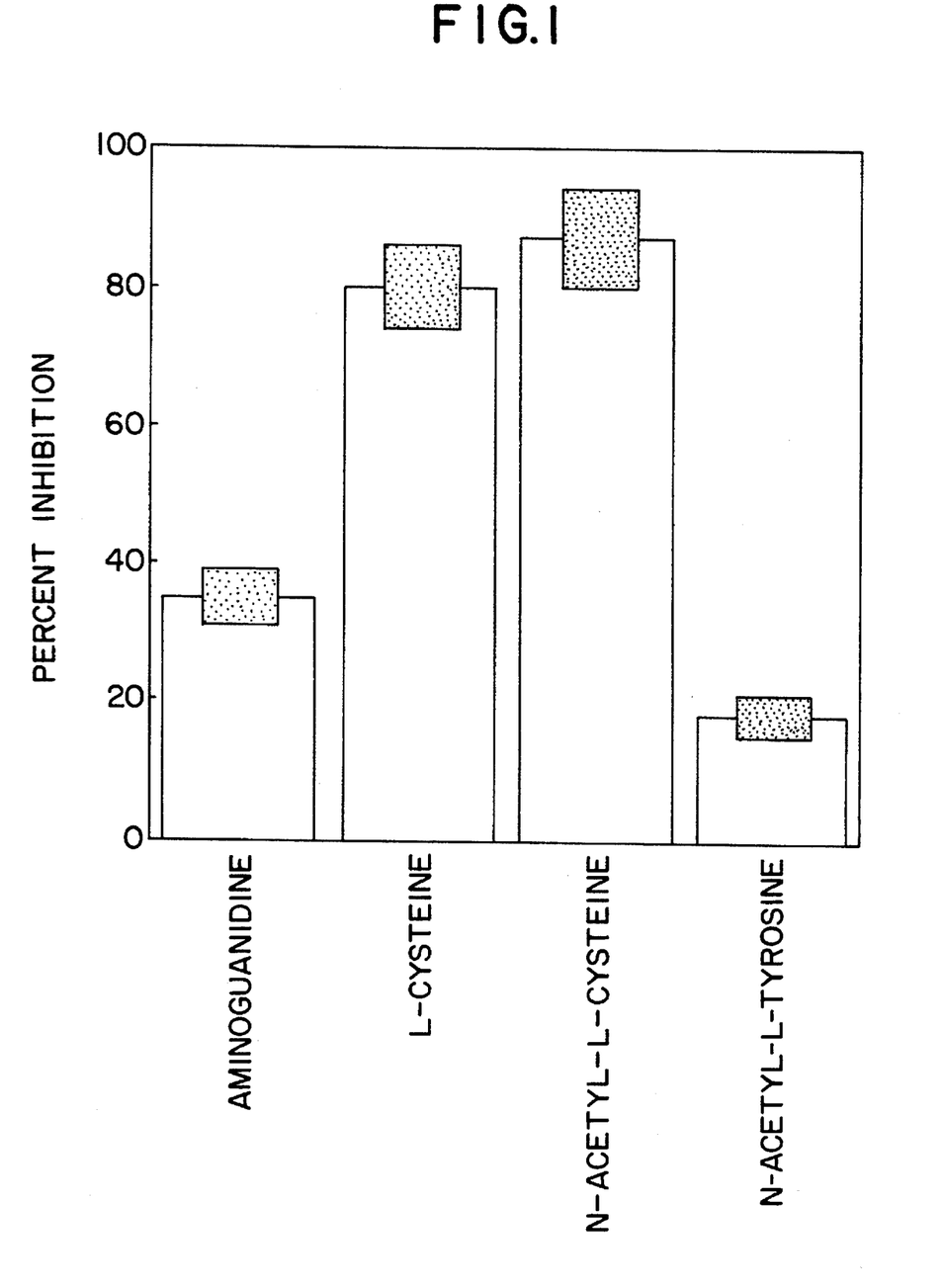
FIG. 1 is a bar graph depicting the results of the percent inhibition of chlorhexidine-accelerated ribose-dependent tooth staining by various agents.
Figure 2:
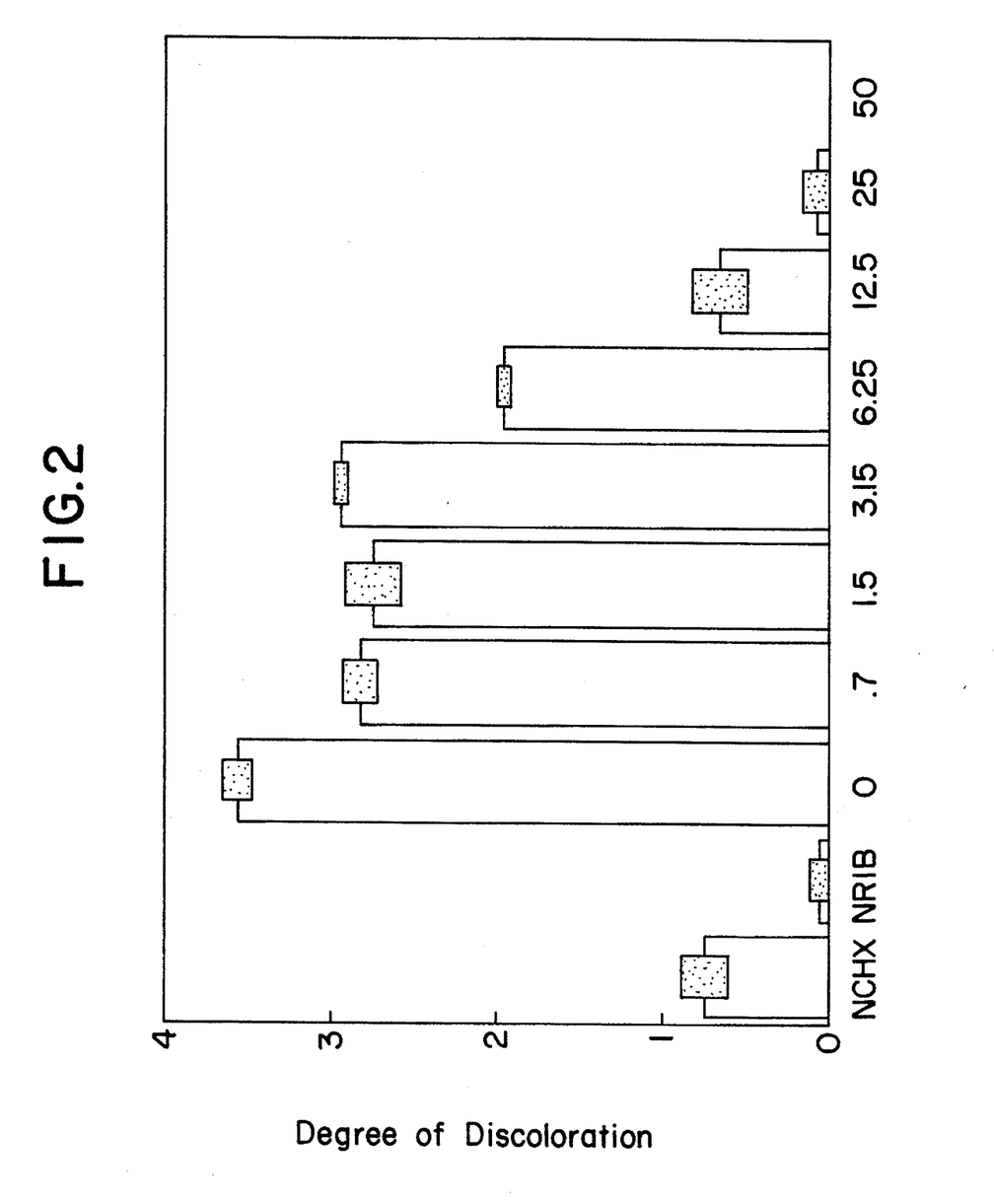
FIG. 2 is a bar graph depicting the degree of discoloration when the chlorhexidine-accelerated ribose-dependent discoloration of oral proteins is inhibited by various amounts of N-acetyl-L-cysteine.

Results are shown in FIGS. 1 and 2.

In the FIG. 1 experiment, aminoguanidine, L-cysteine, N-acetyl-L-cysteine and N-acetyl-L-tyrosine (another amino acid) were tested at 33 millimolar L-cysteine (cysteine) and N-acetyl-L-cysteine (acetylcysteine) both inhibited the CHX-accelerated staining significantly at this dose, while aminoguanidine was much less effective. N-acetyl-L-tyrosine inhibited the discoloration only slightly, suggesting that the acetyl group is not primarily responsible for the activity of N-acetyl-L-cysteine.

In the experiment illustrated by FIG. 2, a dose response comparison is given for N-acetyl-L-cysteine. In the absence of chlorhexidine ("NCHX") or ribose ("NRIB"), very little discoloration occurs. However, when both are present, significant discoloration occurs(O/mM acetylcysteine). Acetylcysteine yields a clear-cut dose-response inhibition with 50% inhibition occurring at approximately 10 millimolar.

In the experiment tabulated below in Table 1, the potency of efficacy of L-cysteine, N-acetyl-L-cysteine, aminoguanidine and three other amino acids (L-arginine, taurine and L-lysine) is compared. The rank order of inhibitory activity is: N-acetyl-L-cysteine>cysteine> aminoguanidine>taurine, arginine>lysine.

TABLE I

COMPARISON OF VARIOUS INHIBITORS OF CHLORHEXIDINE ACCELERATED RIBOSE-DEPENDENT TOOTH STAINING

| COMPOUND | DOSE | PERCENT INHIBITION |
|---|---|---|
| N-ACETYL-L-CYSTEINE | 100 mM | 100 +/– 0 |
|  | 33 mM | 90 +/– 6.4 |
|  | 11 mM | 77 +/– 4.3 |
| L-CYSTEINE | 100 mM | 100 +/– 0 |
|  | 33 mM | 78 +/– 2.6 |
|  | 11 mM | 67 +/– 4.5 |
| TAURINE | 100 mM | 57 +/– 7.0 |
|  | 33 mM | 43 +/– 6.9 |
|  | 11 mM | 26 +/– 3.9 |
| L-ARGININE | 100 mM | 63 +/– 9.5 |
|  | 33 mM | 37 +/– 5.4 |
|  | 11 mM | 27 +/– 3.7 |
| L-LYSINE | 100 mM | 50 +/– 12.0 |
|  | 33 mM | 37 +/– 5.4 |
|  | 11 mM | 7 +/– 7 |
| AMINOGUANIDINE | 100 mM | 74 +/– 12.1 |
|  | 33 mM | 37 +/– 5.4 |
|  | 11 mM | 4 +/– 4.0 |

EXAMPLE 2

Advanced Glycation Endproduct (AGE) Crosslinking Assay

The basis of this assay is the detection by an antibody to AGEs of crosslinks which occur between collagen adsorbed to a microtiter plate and AGE-bovine serum albumin in the solution phase. Aminoguanidine inhibits this process by 50% at a concentration of 10 millimolar.

Results are shown in FIGS. 3 and 4 which indicate that L-cysteine and N-acetyl-L-cysteine approximately equal activity to that of aminoguanidine at 10 millimolar, namely 50% inhibition of crosslinking formation.

EXAMPLE 3

Reversal Experiments

For these experiments, numerous membranes were prestained under the conditions described in Example 1 above. The protein circles were then cut in half with scissors with half of the protein incubated in the presence of a compound in 0.33M phosphate buffer and the other half in buffer alone. During the reversal phase, no ribose or CHX was presented and these incubations typically were carried out for 24 hours.

Stock solutions of compounds were prepared at a variety of concentrations in distilled water and added to the above wells to assess inhibitory activity.

Following the staining reaction, membranes are briefly rinsed in water, blotted dry and tissue and placed in the transparent pockets of slide holders (Kodak). The degree of discoloration is assessed by a blinded fashion against a panel of pre-stained reference filters where:

0=no color, membrane completely white

1=pale yellow color just visible

2=obvious pale yellow

3=yellow

4=dark yellow

5=dark brownish yellow

In some cases, data is converted to "PERCENT INHIBITION". Unless otherwise stated data are mean of quadruplicate determinations +/– standard error of the mean.

Figure 5:
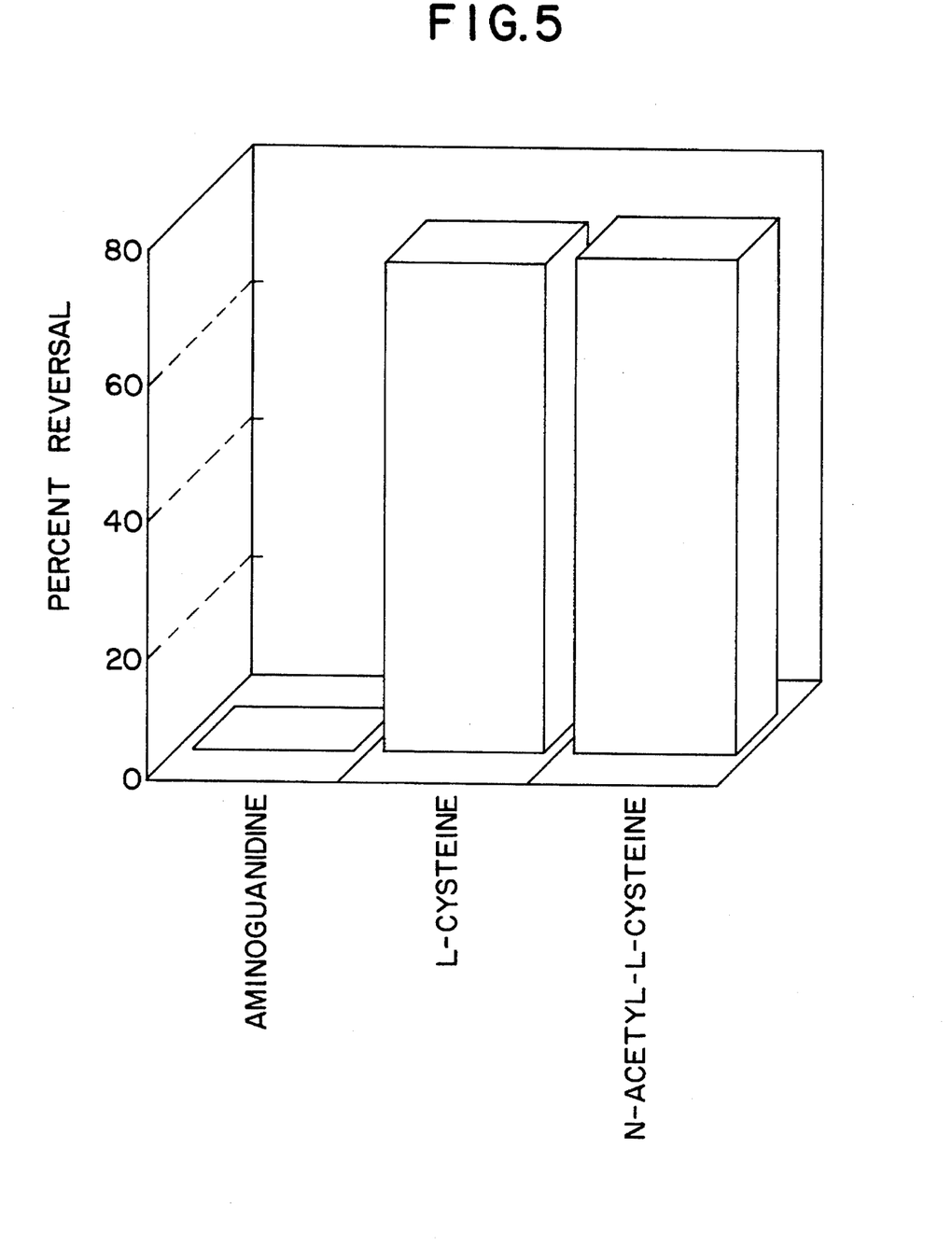
FIG. 5 is a comparison of the reversal of chlorhexidine-induced ribose-dependent toothstaining by N-acetyl-L-cysteine and aminoguanidine.
Figure 6:
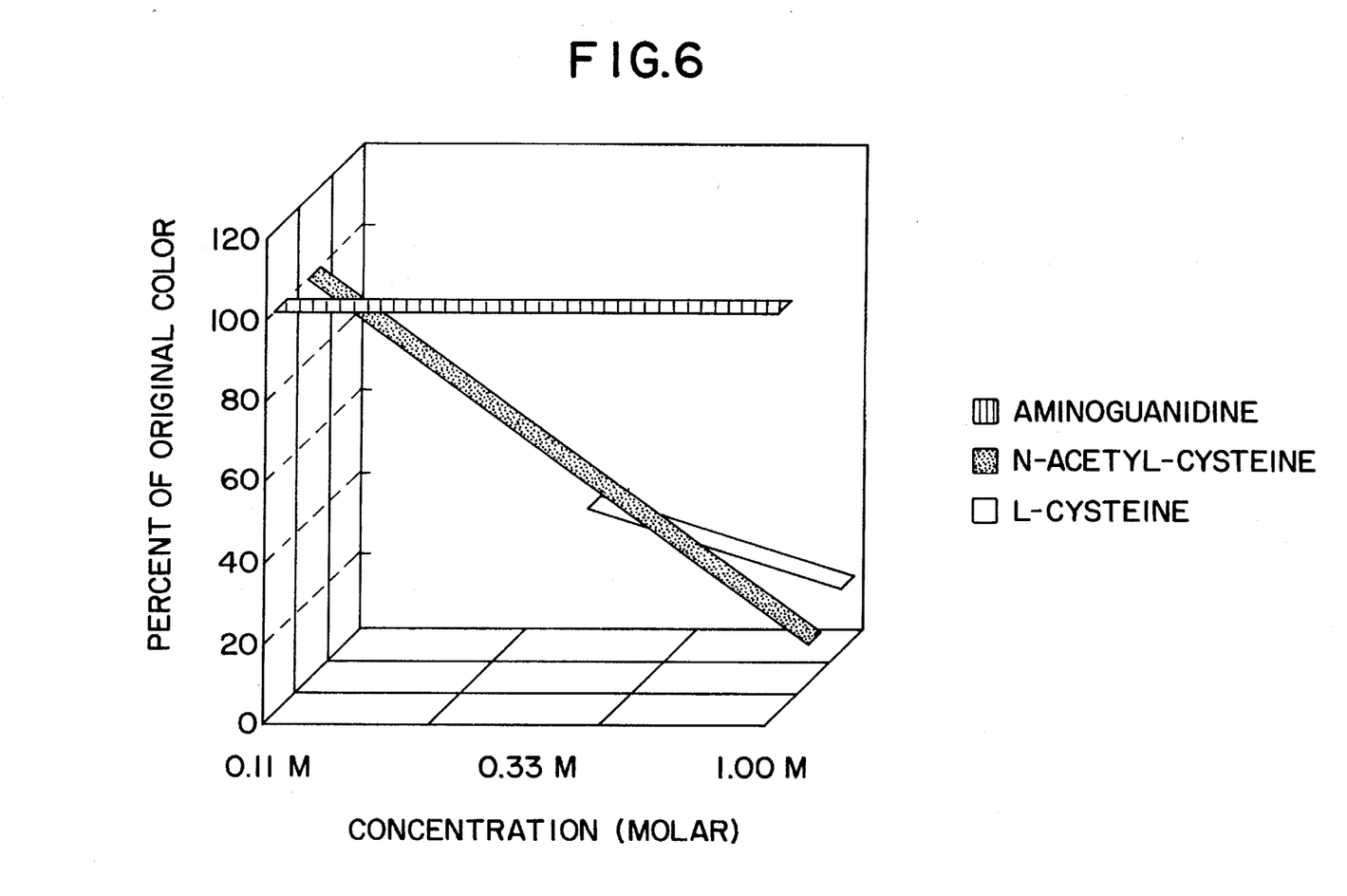
FIG. 6 is a bar graph comparison of the reversal of chlorhexidine-induced tooth-staining by aminoguanidine, L-cysteine and N-acetyl-L-cysteine.

The results are shown in FIG. 5 and 6.

In the results shown in FIG. 5, L-cysteine and N-acetyl-L-cysteine reversed the majority of the staining at 1.0M, exhibiting a dose response effect. Aminoguanidine, on the other hand, did not reverse the CHX-accelerated staining at equivalent concentrations.

In the experiment graphed in FIG. 6, L-cysteine and N-acetyl-L-cysteine, after 24 hours at 1.0M, both induced significant (75%) decolorization while aminoguanidine failed to do so.

In the results shown in Table 2 below, the two chiral forms, as well as the racemic mixture, of cysteine were found to exhibit comparable inhibition of staining in testing

TABLE 2

CHLORHEXIDINE TOOTH STAINING IS INHIBITED BY ALL FORMS OF CYSTEINE

| COMPOUND | PERCENT INIBITION |
|---|---|
| AMINOGUANIDINE | 34.7 +/– 7.5 |
| DL-CYSTEINE HCL | 63.9 +/– 3.1 |

TABLE 2-continued

CHLORHEXIDINE TOOTH STAINING IS INHIBITED BY ALL FORMS OF CYSTEINE

| COMPOUND | PERCENT INIBITION |
|---|---|
| HYDRATE | |
| DL-CYSTEINE HCL ANHYDROUS | 67.3 +/− 3.6 |
| L-CYSTEINE HCL MONOHYDRATE | 70.6 +/− 3.1 |
| L-CYSTEINE HCL ANNYDROUS | 80.4 +/− 6.6 |
| D-CYSTEINE HCL MONOHYDRATE | 60.8 +/− 13.1 |

All compounds tested at 33 millimolar data are mean +/− SEM of quadruplicates

EXAMPLE 4

| Oral Rinse Containing Chlorhexidine and L-Cysteine: | |
|---|---|
| L-Cysteine | 1.4% |
| Chlorhexidine gluconate | 0.12% |
| Ethanol | 11.6% |
| Sodium saccharin | 0.15% |
| FD&C Blue No. 1 | 0.001% |
| Peppermint Oil | 0.5% |
| Glycerine | 10.0% |
| Tween 60 | 0.3% |
| Water to | 100% |

EXAMPLE 5

| Toothpaste Containing L-Cysteine: | |
|---|---|
| L-Cysteine | 5.5% |
| Sorbitol, 70% in water | 25% |
| Sodium saccharin | 0.15% |
| Sodium lauryl sulfate | 1.75% |
| Carbopol 934, 6% dispersion in water | 15% |
| Oil of Spearmint | 1.0% |
| Sodium hydroxide, 50% in water | 0.76% |
| Dibasic calcium phosphate dehydrate | 45% |
| Water to | 100% |

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of inhibiting and reversing the discoloration of teeth and tongue resulting from nonenzymatic browning in the oral cavity which comprises administration to a subject in need of such therapy an amount effective to inhibit said discoloration of a composition comprising cysteine or a cysteine derivative of formula I $$HS-CH_2-\underset{\underset{NHR}{|}}{CH}-COOH \quad (I)$$

wherein R is hydrogen or an acyl group; or a pharmaceutically acceptable salt thereof.

2. The method according to claim 1 wherein said discoloration of teeth and tongue is induced by the use of anti-plaque agent.

3. The method according to claim 2 wherein the anti-plaque agent is chlorhexidine.

4. The method of claim 1, comprising the administration of a composition comprising L-cysteine.

5. The method of claim 1, comprising the administration of a composition comprising N-acetyl-L-cysteine.

6. The method of claim 1, wherein the composition is formulated as an oral rinse.

7. The method of claim 6, wherein the composition additionally contains an anti-plaque agent.

8. The method of claim 7, wherein the anti-plaque agent is chlorhexidine.

9. The method of claim 1, wherein the composition is formulated as a toothpaste.

10. The method of claim 9, wherein the composition additionally contains an anti-plaque agent.

11. The method of claim 10, wherein the anti-plaque agent is chlorhexidine.

* * * * *